United States Patent [19]

Orshitzer et al.

[11] 4,012,341

[45] Mar. 15, 1977

[54] UNIQUE ALL SYNTHETIC DETERGENT SHAMPOO BAR

[75] Inventors: Philip Orshitzer, Staten Island, N.Y.; Antoni Macander, Ridgefield, N.J.

[73] Assignee: American Cyanamid Company, Stamford, Conn.

[22] Filed: June 24, 1975

[21] Appl. No.: 589,968

[52] U.S. Cl. .............................. 252/548; 252/174; 252/550; 252/DIG. 13; 252/DIG. 16

[51] Int. Cl.² ................. C11D 1/83; C11D 1/70; C11D 1/14

[58] Field of Search ............ 252/90, 174, DIG. 16, 252/DIG. 13, 550, 548; 424/70

[56] References Cited

UNITED STATES PATENTS

| | | | |
|---|---|---|---|
| 2,756,178 | 7/1956 | Verblen | 252/DIG. 13 X |
| 2,950,255 | 8/1960 | Goff | 252/DIG. 13 X |
| 3,081,267 | 3/1963 | Laskey | 252/DIG. 16 |
| 3,129,187 | 4/1964 | Meehan | 252/155 |
| 3,318,817 | 5/1967 | Smith | 252/DIG. 16 |
| 3,798,181 | 3/1974 | Vazquez | 252/DIG. 16 |
| 3,903,008 | 9/1975 | Deweever et al. | 252/DIG. 13 X |

*Primary Examiner*—Harris A. Pitlick
*Attorney, Agent, or Firm*—Charles J. Fickey

[57] ABSTRACT

Synthetic all detergent shampoo bar in which a mixture of an anionic and non-ionic detergent comprises the major components and which has controlled water solubility, good foaming action and rinsability provides body and conditions the hair.

3 Claims, No Drawings

UNIQUE ALL SYNTHETIC DETERGENT SHAMPOO BAR

This invention relates to an all synthetic detergent composition having superior properties which can be shaped into bars. More particularly, this invention relates to a synthetic all detergent shampoo bar in which a mixture of an anionic and non-ionic detergent comprise the major components and which has controlled water solubility, good foaming action and rinsability provides body and conditions the hair.

Synthetic detergents, particularly alkyl aryl sulfonates, have rapidly replaced soap as general cleaning agents. They have been prepared and marketed as powdered, granular and liquid forms. Synthetic detergents in the form of toilet bars have not met with any commercial success. Meehan, U.S. Pat. No. 3,129,187 discloses a synthetic detergent toilet bar which reportedly gives a "soapy" feel, has good rinsability and sudsing properties, is non-hygroscopic, does not become soft and slushy in use, and leaves the skin feeling smooth, soft and tack free. The major component in an anionic detergent (sodium alkyl benzene sulfonate) combined with a long chain alcohol (stearyl, cetyl), a wax (n-paraffin), an alkanolamide (monoethanolamide or stearic acid), and water.

The present invention is based on a novel "all detergent" shampoo composition having a major proportion of a mixture of an anionic detergent and a non-ionic detergent and a minor amount of a binder material, shaped into the form of a hard bar which exhibitis controlled water solubility, excellent foam characteristics, good rinsability, and providing body and conditioning to the hair.

The shampoo bar composition of this invention comprises a mixture of from about 10 to 60 parts by weight, preferably 15 to 40 parts by weight, of a polyethoxylated dialkyl phenol non-ionic detergent, from about 30 to 60 parts by weight, preferably 40 to 55 parts by weight, of a sodium or potassium higher alkyl sulfate ($C_{12}$ to $C_{20}$), preferably sodium lauryl sulfate anionic detergent, and from about 10 to 40 parts by weight, preferably 15 to 30 parts by weight, of the monoethanolamide of stearic acid as a binding agent.

All of the components of the composition of this invention are solid materials at room temperature. For example, a polyethoxylated dialkyl phenol marketed under the trade name, IGEPAL DM-970 is a unique, highly water soluble, solid, high melting compound, derived from the ethoxylation of a higher ($>C_8$) alkyl phenol. It or similar ethoxylated dialkylphenols which are water soluble, high melting solids are useful as the non-ionic detergent component of the shampoo bar. The amount of the non-ionic ethoxylated alkylphenol will vary from about 10 percent by weight to about 60 percent by weight, although we prefer to use 15 to 25 percent by weight. When the shampoo bar composition contains less than about 10 percent of the ethoxylated dialkylphenol, the bar becomes fragile and when greater than about 60 percent, the bar becomes soggy in contact with water.

The anionic detergent is sodium or potassium higher alkyl sulfate ($C_{12}$–$C_{20}$), preferably sodium lauryl sulfate, which provides foaming. Sodium lauryl sulfate is a solid compound which is water soluble, forming an opalescent solution. It is one of the major anionic detergents used in shampoo compositions although it is normally employed at a level of 5–15 percent by weight on an anhydrous basis. In the present invention sodium lauryl sulfate is used as the dry solid at a concentration of from about 30 to 60 percent by weight, although we prefer to use from about 40 to 55 percent by weight. When less than about 30 weight percent is used the bar produces low foam and when more than about 60 weight percent is used the bar disintegrates or dissolves rapidly. Mixtures of the higher alkyl sulfates with alkali metal alkylaryl sulfonates are also useful.

The third essential component of the composition is a fatty acid ($C_{14}$–$C_{20}$) monoethanolamide, preferably stearic acid, monoethanolamide, which is marginally a non-ionic detergent compound having a high melting point (87° C.). It is normally used in liquid shampoo compositions only as an additive to stabilize lather and viscosity, and generally used in such cases at a level of about 3 to 5 percent by weight. In the present invention the compound is used as a binder for the anionic and non-ionic detergents and to provide a high degree of hardness and to control water solubility of the shampoo bar. It is used at a concentration ranging from about 10 to 40 percent by weight, although we prefer to use 15 to 30 percent by weight. When less than about 10 weight percent is used, disintegration in water increases and when more than about 40 weight percent is used in flash foam decreases.

The desirable features of the shampoo bar of this invention are provided by a combination of good foaming characteristics of the alkali metal higher alkyl sulfate; e.g. sodium lauryl sulfate, the water insolubility, hardness and binding capacity of the fatty acid monoethanolamide, e.g. stearic acid monoethanolamide, and the good foaming and hardness characteristics of the polyethoxylated dialkyl phenol.

The solid detergent shampoo bar of this invention is readily prepared by heating a mixture of the ethoxylated dialkylphenol and the monoethanolamide of stearic acid to about 100° C., adding a dye, if desired, to the mixture and then adding the solid sodium lauryl sulfate thereto using a high speed mixer. When the composition is smooth a perfume may be added (optional) and the resulting composition put several times through a grinder and finally molded under pressure into the form of a bar.

Water solubility is determined as the time for 0.5 gram of the shampoo composition to dissolve in 100 ml. deionized water when stirred at 200 RPM.

Foam height is determined by separately shaking 0.5 gram of the composition in 100 ml. of water containing 40 ppm of calcium carbonate and deionized water in a graduated cylinder and measuring the height of the foam in ml.

The following specific examples are illustrative of the invention.

EXAMPLE 1

A synthetic detergent shampoo bar was formulated using the following ingredients:
Sodium lauryl sulfate: 54
Ethoxylated alkylphenol: 17
Monoethanolamide of stearic acid: 26
Perfume: 2
Dye: 1

Bars prepared as described were evaluated and found to provide quick lather, good hardness in contact with water, good hair cleansing properties and good rinsability.

One half gram of the above composition dissolved in 100 ml. deionized water in 20 minutes when stirred at 200 RPM. Foam height was about 60 ml. in either deionized water or water containing 40 ppm calcium carbonate.

Examples 2 to 4 illustrate additional examples of the invention which were prepared as in Example 1 and were similarly effective.

EXAMPLE 2

Sodium lauryl sulfate (90% active): 50.0
Ethoxylated alkylphenol: 23.0
Monoethanolamide of stearic acid: 23.0
Perfume: 2.0
Dye (D&C Green No. 5; 0.4% soln.): 1.0
Polymer JR-400 (Union Carbide): 1.0

EXAMPLE 3

Sodium lauryl sulfate (90% active): 34.0
Sodium dodecyl benzene sulfonate: 21.0
Ethoxylated alkylphenol: 21.0
Monoethanolamide of stearic acid: 21.0
Perfume: 1.6
Dye (D&C Green No. 5; 0.4% soln.): 1.4

EXAMPLE 4

Sodium lauryl sulfate (90% active): 50.0
Ethoxylated alkylphenol: 21.5
Monoethanolamide of stearic acid: 21.5
Perfume: 2.0
Dye (D&C Green No. 5; 0.4% soln.): 1.0
Polyvinyl alcohol (VINOL 533): 3.0
Polymer JR-400: 1.0

We claim:

1. A solid all synthetic detergent shampoo bar comprising from about 10–60% of a water soluble, solid, polyethoxylated dialkyl phenol wherein each of the alkyl groups contain more than 8 carbon atoms; from about 30–60% of a sodium or potassium higher alkyl sulfates wherein the alkyl group contains between 12 and 20 carbon atoms; and from about 10–40% of the monoethanolamide of stearic acid.

2. A detergent shampoo bar according to claim 1 wherein said composition comprises from about 15–25% of said water-soluble, solid, polyethoxylated dialkyl phenol; from about 40–55% of said sodium or potassium higher alkyl sulfates; and from about 15–30% of said monoethanolamide of stearic acid.

3. A detergent shampoo bar according to claim 2 wherein said sodium or potassium higher alkyl sulfate is sodium lauryl sulfate.

* * * * *